(12) United States Patent
Milanese et al.

(10) Patent No.: US 9,962,372 B2
(45) Date of Patent: May 8, 2018

(54) PHARMACEUTICAL COMPOSITION FOR THE TREATMENT OF MYCOSIS

(71) Applicant: AZIENDE CHIMICHE RIUNITE ANGELINI FRANCESCO A.C.R.A.F. S.p.A., Rome (IT)

(72) Inventors: Claudio Milanese, Rome (IT); Alessandra Capezzone De Joannon, Rome (IT); Serena Tongiani, Genzano di Roma (IT); Luca Donati, Porto San Giorgio (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 0 days. days.

(21) Appl. No.: 15/541,245

(22) PCT Filed: Jan. 8, 2016

(86) PCT No.: PCT/EP2016/050272
§ 371 (c)(1),
(2) Date: Jun. 30, 2017

(87) PCT Pub. No.: WO2016/113194
PCT Pub. Date: Jul. 21, 2016

(65) Prior Publication Data
US 2018/0000783 A1 Jan. 4, 2018

(30) Foreign Application Priority Data
Jan. 13, 2015 (EP) .................................... 15150904

(51) Int. Cl.
*A61K 31/416* (2006.01)
*A61K 9/06* (2006.01)
*A61K 31/4196* (2006.01)
*A61K 31/4174* (2006.01)

(52) U.S. Cl.
CPC .............. *A61K 31/416* (2013.01); *A61K 9/06* (2013.01); *A61K 31/4174* (2013.01); *A61K 31/4196* (2013.01)

(58) Field of Classification Search
CPC .... A61K 31/416; A61K 9/06; A61K 31/4174; A61K 31/4196
USPC ....................................................... 514/383
See application file for complete search history.

(56) References Cited

U.S. PATENT DOCUMENTS

2004/0180965 A1* 9/2004 Borgman ............. A61K 9/0034
514/649
2009/0208558 A1 8/2009 Noe et al.

FOREIGN PATENT DOCUMENTS

WO 96/26724 A1 9/1996

OTHER PUBLICATIONS

Rani et al. Mini-reviews in Medicinal chemistry, 2013, 13(11), 1626-1655 (abstract).*
Yucesoy et al., "In-vitro Synergistic Effect of Fluconazole with Nonsteroidal Anti-Inflammatory Agents Against *Candida albicans* Strains", Journal of Chemotherapy, vol. 12, No. 5, 2000, p. 385-389, XP 002429141.
Boselli et al., "Efficacy and Tolerability of Fitostimoline (Vaginal Cream, Ovules, and Vaginal Washing) and of Benzydamine Hydrochloride (Tantum Rosa Vaginal Cream and Vaginal Washing) in the Topical Treatment of Symptoms of Bacterial Vaginosis", ISRN Obstetrics and Gynecology, vol. 2012, 2012, p. 1-5.
EUCAST, "EUCAST Definitive Document EDef 7.1: method for the determination of broth dilution MICs of antifungal agents for fermentative yeasts", Clinical Microbiology and Infection, vol. 14, No. 4, Apr. 2008, 8 pages.
Franz, "Percutaneous Absorption. On the Relevance of In Vitro Data", The Journal of Investigative Dermatology, vol. 64. No. 3, 1975, p. 190-195.
Meletiadis et al., "Defining Fractional Inhibitory Concentration Index Cutoffs for Additive Interactions Based on Self-Drug Additive Combinations, Monte Carlo Simulation Analysis, and In Vitro-In Vivo Correlation Data for Antifungal Drug Combinations against *Aspergillus fumigatus*", Antimicrobial Agents and Chemotherapy, vol. 54. No. 2, 2010, 9 pages.
International Search Report dated Mar. 2, 2016, in PCT/EP2016/050272, filed Jan. 8, 2016.
Rani et al., "Imidazoles as Potential Antifungal Agents: A Review", Mini-Reviews in Medicinal Chemistry, vol. 13, 2013, p. 1626-1655, XP 9183599A.
Moody et al., "In Vitro Activities of Miconazole, Miconazole Nitrate, and Ketoconazole Alone and Combined with Rifampin Against *Candida* spp. And *Torulopsis glabrata* Recovered from Cancer Patients". Antimicrobial Agents and Chemotherapy, vol. 17, No. 5, May 1980, p. 871-875, XP 55180997A.
Stelmachow et al., "Efficacy and tolerance of benzydamine in the treatment of vaginal infections", Medical Science Monitor, vol. 4, No. 6, 1998, p. 1040-1042, XP 009183593.

* cited by examiner

*Primary Examiner* — Yevgeny Valenrod
(74) *Attorney, Agent, or Firm* — Oblon, McClelland, Maier & Neustadt, L.L.P.

(57) ABSTRACT

The present invention relates to a pharmaceutical composition comprising a combination of benzydamine and an antimycotic active ingredient, said combination having a synergistic effect in the treatment of mycosis.

16 Claims, 1 Drawing Sheet

PHARMACEUTICAL COMPOSITION FOR THE TREATMENT OF MYCOSIS

FIELD OF THE INVENTION

The present invention relates to a pharmaceutical composition comprising a combination of benzydamine and an antimycotic active ingredient, said combination having a synergistic effect in the treatment of mycosis.

BACKGROUND OF THE INVENTION

Fungi belonging to the genus *Candida* are one of the most common causes of fungal infections worldwide.

Many species of *Candida* are harmless commensals or endosymbionts of their hosts, such as for example human beings.

Fungi belonging to the species *Candida albicans* and *Candida tropicalis* are normally present on the mucosa of oral cavity, gastro-intestinal tract and vagina. However, when the flora of the mucosae is altered, for example due to long treatment with antibiotics or hormonal changes, fungi can abnormally multiply and cause superficial infections, for example in the mouth or in the vagina, known as candidiasis. In immunosuppressed people, fungi can even cause severe systemic infections, known as candidemia, that are sometimes deadly.

Vulvovaginitis caused by fungi represents today about 30-35% of vaginal infections and is mostly caused by *Candida albicans* fungi.

Vulvovaginitis is accompanied by changes of the vaginal pH and the main symptoms are intense vaginal and/or vulvar itching, leakages, inflammation and pain.

Typically, the treatment is by administration of topical antimycotic drugs in form of creams, vaginal ovules and solutions for external use. In case of severe and/or relapsing infections, antimycotic drugs are administered orally.

Pevaryl™ is a commercially available cream for the treatment of vulvovaginal mycosis, containing 1% w/w of econazole nitrate.

Econazole is an imidazole derivative, endowed with a broad spectrum antimycotic activity and commonly used for the treatment of *Candida albicans* mycosis.

Several patent applications disclose combinations of active ingredients useful in the treatment of oral and vulvovaginal mycosis.

WO 96/26724 discloses a pharmaceutical composition comprising an anti-inflammatory amount of benzydamine or a salt thereof, an antimicrobially effective amount of an antimicrobial agent and a pharmaceutically acceptable carrier or excipient.

US 2009/0208558 relates to the use of an antimycotic agent and an epithelial cell or endothelial cell adhesion inhibitor for producing a combination drug for the topical treatment of *Candida* mycosis.

Most drug combinations show an additive effect. In some instances however, the combinations show less or more than an additive effect. These combinations are called antagonistic or synergistic, respectively. Antagonistic or synergistic effects are unpredictable, and are unexpected experimental findings. Finding highly efficacious combinations, i.e., synergistic mixtures, of active agents is challenging however. Serendipity is not a valid route as the number of potential combinations of agents is staggeringly large. The other normal discovery strategy of deducing potential combinations from knowledge of mechanism is also limited in its potential because many biological end points of living organisms are affected by multiple pathways. These pathways are often not known, and even when they are, the ways in which the pathways interact to produce the biological end effect are often unknown.

SUMMARY OF THE INVENTION

The Applicant faced the problem to provide a pharmaceutical composition for the treatment of mycosis, having an improved activity when compared to the compositions known in the art.

The Applicant has found that benzydamine can be used in association with antimycotic active ingredients derived from imidazole.

In particular, the Applicant has now surprisingly found that the combination of benzydamine with an antimycotic active ingredient derived from imidazole has a synergistic effect in inhibiting the growth of fungi belonging to genus *Candida*.

Thus, in a first aspect, the present invention relates to a pharmaceutical composition comprising a combination of benzydamine and an imidazole-antimycotic or a salt thereof, and at least one pharmaceutically acceptable excipient, for use in the treatment of *Candida* mycosis.

Advantageously, benzydamine in the composition according to the present invention gives relief from vulvovaginal itching and pain.

Preferably, said imidazole-antimycotic is selected in the group comprising bifonazole, butoconazole, chlormidazole, clotrimazole, croconazole, econazole, fenticonazole, ketoconazole, isoconazole, miconazole, neticonazole, omoconazole, oxiconazole, sertaconazole, sulconazole, tioconazole or salts thereof.

More preferably, said imidazole-antimycotic is selected in the group comprising bifonazole, butoconazole, clotrimazole, econazole, fenticonazole, ketoconazole, isoconazole, miconazole, omoconazole, sertaconazole, sulconazole, tioconazole or salts thereof.

Even more preferably, said imidazole-antimycotic is selected in the group comprising butoconazole, econazole, fenticonazole, isoconazole, miconazole, sulconazole or salts thereof.

Advantageously, said imidazole-antimycotic is econazole, miconazole or a salt thereof.

Preferably, said *Candida* mycosis is caused by *Candida Albicans, Candida lusitaniae, Candida tropicalis, Candida glabrata, Candida. rugosa, Candida parapsilosis, Candida tropicalis*, or *Candida dubliniensis*. More preferably, said *Candida* mycosis is caused by *Candida Albicans, Candida lusitaniae*, or *Candida tropicalis*.

More preferably, said *Candida* mycosis is mucosal candidiasis, cutaneous candidiasis, onychomycosis, systemic candidiasis, iatrogenic candidiasis, diaper candidiasis, intestinal candidiasis or *candida* balanitis.

Even more preferably, said mucosal candidiasis is oral or vulvovaginal.

DETAILED DESCRIPTION OF THE INVENTION

Figure 1:
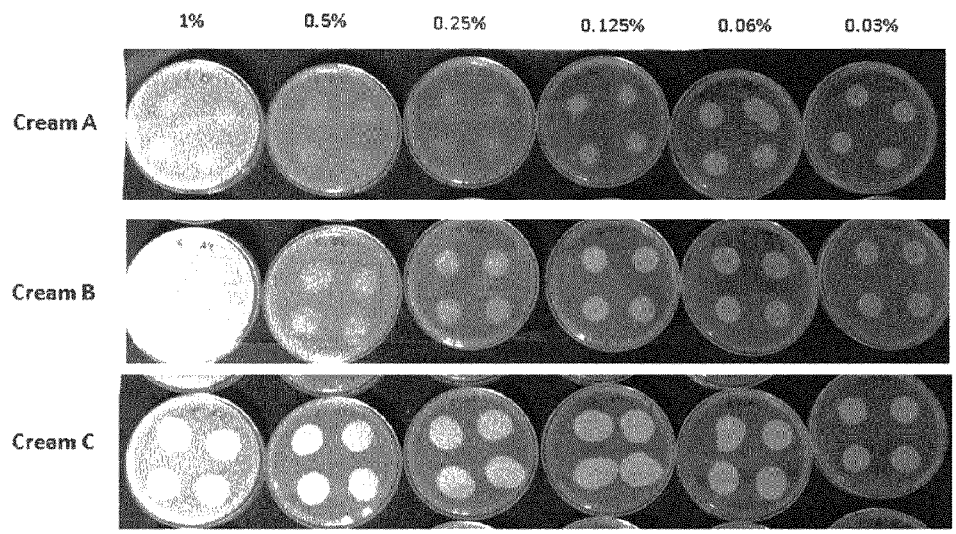
FIG. 1 visually shows the results of the activity of creams A to C of example 7 tested on plates containing *Candida albicans* strain ATCC 10231 with the agar dilution method using from 1% to 0.03% w/v of cream.

In the present description, the expression "synergistic effect" means that the combination of benzydamine and of the imidazole-antimycotic inhibits the growth of a strain of fungi belonging to the genus *Candida* at a concentration lower than the sum of the concentrations of benzydamine and of the antimycotic-imidazole used alone for the same strain to obtain the same inhibition. In other words, a synergistic effect means that the combination of benzydamine and of the imidazole-antimycotic is effective in producing more than the additive effect of each component in the same strain.

Synergy is defined herein in terms of the fractional inhibitory concentration (FIC) index, which is the sum of the FIC's for the individual drugs used in each combination, as described by Meletiadis J. et al. in Antimicrobial Agents and Chemotherapy, February 2010, p. 602-609. Under a strict scientific, and preferred, definition synergy is defined by a FIC index of less than 0.5, i.e., when 50% inhibition results from a combination of one-fourth or less of the concentration of each drug required to elicit the same effect if used individually (i.e., the minimal inhibiting concentration (MIC) of each drug). An FIC index of 0.5 under this strict definition defines an additive response. Under a broader definition used for purposes herein synergistically effective amounts are defined by an FIC index of less than 1.0, i.e., when 50% inhibition results from a combination of one-half or less of the MIC of each drug. An FIC index of 1.0 under this broader definition defines an additive response. Under this test, isobolograms may be prepared from the dose response curves for various combinations of benzydamine and antimycotic-imidazole in each strain, with synergy indicated by points below the line which line connects the FIC index of 1 for benzydamine with the FIC index of 1 for antimycotic-imidazole. This standard allows one to determine the MIC's for the combinations tested, so as to provide the MIC of each component needed to achieve a synergistic mixture. The exact amounts will depend, for example, on the particular strain.

In the present description and in the following claims, the expression "imidazole-anti mycotic" indicates antimycotic active ingredients comprising an imidazole ring in their chemical structure.

Preferably, the pharmaceutical composition according to the present invention contains benzydamine in an amount from 0.001 wt. % by weight to 1 wt. % by weight, more preferably from 0.05 wt. % to 0.5 wt. %, and even more preferably from 0.08 wt. % to 0.2 wt. %.

Preferably, the pharmaceutical composition according to the present invention contains the imidazole-antimycotic, or a salt thereof, in an amount from 0.01 wt. % to 4 wt. % of, more preferably from 0.1 wt. % to 2 wt. % and even more preferably from 0.5 wt. % to 1.5 wt. %.

Preferably, the pharmaceutical composition according to the present invention is for topical use.

Preferably, the pharmaceutical composition according to the present invention is prepared in suitable dosage forms, such as creams, ointments, lotions, gel, foams, ovules, prolonged release ovules, vaginal douches, or solutions for external use.

More preferably, said dosage form is cream, ointment, lotion, vaginal douche or solution for external use.

Even more preferably, said dosage form is cream or vaginal douche.

The pharmaceutically acceptable excipient can be selected from the group comprising: emollients, thickeners, preservative, stabilizers, surfactants, buffers, salts for regulating osmotic pressure, emulsifiers and the like.

Preferably, the pharmaceutical composition according to the present invention comprises one or more emulsifier having a HLB ranging from 6 to 9 and one or more emulsifier having a HLB ranging from higher than 9 to 12.

Emulsifiers having a HLB ranging from 6 to 9 useful in the present invention are, for example, cetearyl alcohol, ceteareth-20, polyglyceryl-3-diisostearate, a mixture of sorbitan stearate and sucrose socoate, PEG-4 dilaurate, methyl glucose sesquistearate, laureth-2, laureth-3, PEG-8 dioleate, polyglyceryl-5-dioleate, sodium stearoyl lactylate, sorbitan laurate, lauroyl macrogol-6 glycerides, PEG-40 sorbitan peroleate, polyglyceryl-3 stearate, polyglyceryl-2 laurate.

Emulsifiers having a HLB ranging from higher than 9 to 12 useful in the present invention are, for example laureth-4, PEG-7 glyceryl cocoate, PEG-20 almond glycerides, polyglyceryl-3 palmitate, PEG-25 hydrogenated castor oil, stearamide, a mixture of glyceryl stearate PEG-100 stearate, polysorbate 85, PEG-7 olivate, cetearyl glucoside, cetearyl olivate, glyceryl monostearate, polyglyceryl-10 diisostearate, polysorbate 85, polyglyceryl-5 oleate, PEG-8 oleate, glyceryl stearate citrate, PEG-7 glyceryl cocoate, polyglyceryl-3 methyglucose distearate.

Particularly preferred emulsifiers having HLB ranging from higher than 9 to 12 are Tefose 63, a mixture of PEG-6 and PEG-32 palmitostearate and glycol stearate, and Gelot 64, a mixture of glycerol monostearate and PEG-75 stearate, both manufactured by Gattefossé SAS, France.

Particularly preferred emulsifiers having HLB ranging from 6 to 9 are Labrafil M2130CS, a mixture of lauroyl macrogol-6 glycerides, and Labrafil M1944CS, a mixture of oleoyl polyoxyl-6 glycerides, both manufactured by Gattefossé SAS, France.

The examples that follow are intended for further illustration of the present invention, though without limiting it.

EXAMPLES

The aim of the tests disclosed in examples 1 to 5 was to assess the in vitro fungicidal activity of the combination of benzydamine and of an imidazole-antimycotic against strains of fungi belonging to genus *Candida*.

Example 1

1.1 Preparation of Fungal Strains

*Candida* strains stored at −80° C. were thawed and streaked on SDA plate and then a second subculture was performed. Then, *Candida* strains suspensions were prepared as follows.

10 ml of saline were placed in a 50 ml falcon tube with 5 g of glass beads. Loopful of the cells of the colonies of the second subculture were transferred into the saline and suspended by rubbing the loop against the wet wall of the tube to dislodge the cells. The tube was then shacked for 3 minutes using a mechanical shaker.

The number of cells in the suspension was adjusted from $1.5 \times 10^6$ to $5.0 \times 10^6$ colony forming units (CFU)/ml using saline according to Mc Farland standard No. 0.5 standard and reading the optical density at 550 nm.

For counting, serially 1:10 dilutions were prepared using saline, to obtain $10^{-4}$ and $10^{-5}$ dilutions of the suspension. A sample of 100 μl of each dilution was spread plate and incubated at 37° C. for 48 h. The number of colonies was counted by visual inspection and the cell density was found to be within the desired range.

1.2 Agar Dilution Method

The methodology was similar to that disclosed by R. Moody et al., "*In Vitro Activities of Miconazole, Miconazole Nitrate, and Ketoconazole Alone and Combined with Rifampin against Candida spp. and Torulopsis glabrata Recovered from Cancer Patients.*", Antimicrobial Agents and Chemotherapy: 1980, 17, 871-875.

1.2.1 Preparation of Active Ingredients Solutions

Standard Petri dishes (92 mm diameter×16 mm height) were used. After the agar was poured, plates were allowed to cool and then immediately used.

(A) The solutions used to calculate the MIC of the active ingredients were prepared as described herein below.

Econazole nitrate and miconazole nitrate were each dissolved in 100% dimethyl sulfoxide (DMSO) to concentrations of 5.0 mg of active drug per ml. Then, serial 1:2 dilutions were prepared in DMSO, to concentrations from 5.0 mg/ml to 0.078 mg/ml. 0.250 ml of each solution of econazole or miconazole nitrate were added to 24.75 ml (1:100 dilution) of molten Sabouraud agar (Difco Laboratoires, Detroit, Mich.), mixed, and poured into standard Petri dishes, to final concentration from 50 µg/ml to 0.78 µg/ml.

Benzydamine was dissolved in water to a concentration of 12.5 mg/ml. Then, serial 1:2 dilutions were prepared in water, to concentrations from 12.5 mg/ml to 1.56 mg/ml. 1 ml of each solution of benzydamine was added to 24 ml (1:25 dilution) of molten Sabouraud agar, mixed, and poured into standard Petri dishes, to final concentration from 0.5 mg/ml to 0.0625 mg/ml.

As positive control, Amphotericin B from a stock solution of 1600 µg/ml was diluted in DMSO to solutions having concentrations from 50 µg/ml to 6.25 µg/ml. These solutions were diluted 1:100 in Sabouraud agar, mixed and poured into standard Petri dishes, to final concentration from 0.5 µg/ml to 0.0625 µg/ml.

Negative controls of water, DMSO and water+DMSO were included in the experiment.

(B) For synergy studies, further solutions of econazole and miconazole nitrate having concentrations from 2.5 mg/ml to 0.098 mg/ml were prepared in DMSO, with serial 1:2 dilutions as disclosed in paragraph 1.2.1(A).

Also, further solutions of benzydamine having concentrations from 6.25 mg/ml to 1.56 mg/ml were prepared in water, with serial 1:2 dilutions as disclosed in paragraph 1.2.1(A). Moreover, the solution of benzydamine with a concentration of 6.25 mg/ml was diluted 1:1.43 in water to give a solution of benzydamine having a concentration of 4.37 mg/ml.

Then, 0.250 ml of each solution of econazole or miconazole nitrate and 1 ml of each solution of benzydamine were added to 23.750 ml of molten Sabouraud agar (Difco Laboratoires, Detroit, Mich.), mixed, and poured into standard Petri dishes, thus resulting in final concentrations of econazole or miconazole from 25 µg/ml to 0.098 µg/ml and of benzydamine from 0.25 mg/ml to 0.0625 mg/ml and 0.175 mg/ml.

1.2.2 Susceptibility Testing (A) For the calculation of the MIC, the surface of each standard Petri dish prepared as described in paragraph 1.2.1(A) was inoculated with four spots (20 µl inoculum volume) of the *Candida* strains suspensions prepared as described in paragraph 1.1.

Test suspensions inoculated onto standard Petri dishes with amphotericin B were used as positive control.

Test suspension inoculated onto standard Petri dishes without drugs but containing water, DMSO and water+DMSO were used as negative controls.

All the Petri dishes were incubated at 35° C. for 48 h.

(B) For synergy studies, the surface of each Petri dish prepared as described in paragraph 1.2.1(B) was inoculated with four spots (20 µl inoculum volume) of the *Candida* strains suspensions prepared as described in paragraph 1.1, and incubated at 35° C. for 48 hours.

1.3 Broth Dilution Method

The methodology used for the broth dilution method was similar to that disclosed in "*EUCAST Definitive Document EDef 7.1: method for the determination of broth dilution MICs of antifungal agents for fermentative yeasts*" (Clin Microbiol Infect 2008; 14: 398-408).

1.3.1 Preparation of Active Ingredients Solutions (A) The solutions used to calculate the MIC of the active ingredients were prepared as described herein below.

Econazole nitrate and miconazole nitrate were each dissolved in 100% dimethyl sulfoxide (DMSO) to concentrations of 10.0 mg of active drug per ml. Then, serial 1:2 dilutions were prepared in DMSO, to concentrations from 10.0 mg/ml to 0.078 mg/ml. These solutions were further diluted 1:100 in RPMI-1640 (GiBCO® by Life Technologies) containing 2% glucose, 3-(N-morpholino) propanesulfonic acid (MOPS, by SIGMA) without $NaHCO_3$, to final concentration from 100 µg/ml to 0.78 µg/ml.

Clotrimazole nitrate was dissolved in 100% dimethyl sulfoxide (DMSO) to concentrations of 1.250 mg of active drug per ml. Then, serial 1:2 dilutions were prepared in DMSO, to concentrations from 1.250 mg/ml to 0.0196 mg/ml. These solutions were further diluted 1:100 in RPMI-1640 (GiBCO® by Life Technologies) containing 2% glucose, 3-(N-morpholino) propanesulfonic acid (MOPS, by SIGMA) without $NaHCO_3$, to final concentration from 12.50 µg/ml to 0.196 µg/ml.

Fluconazole nitrate was dissolved in 100% dimethyl sulfoxide (DMSO) to concentrations of 5.0 mg of active drug per ml. Then, serial 1:2 dilutions were prepared in DMSO, to concentrations from 5.0 mg/ml to 0.3125 mg/ml. These solutions were further diluted 1:100 in RPMI-1640 (GiBCO® by Life Technologies) containing 2% glucose, 3-(N-morpholino) propanesulfonic acid (MOPS, by SIGMA) without $NaHCO_3$, to final concentration from 50 µg/ml to 3.125 µg/ml.

Benzydamine was dissolved in water to a concentration of 25 mg/ml. Then, serial 1:2 dilutions were prepared in water, to concentrations from 25 mg/ml to 3.125 mg/ml. 1 ml of each solution was added to 24 ml (1:25 dilution) of RPMI-1640 (GiBCO® by Life Technologies) containing 2% glucose, 3-(N-morpholino) propanesulfonic acid (MOPS, by SIGMA) without $NaHCO_3$, to final concentration from 1 mg/ml to 0.125 mg/ml.

As positive control Amphotericin B from a stock solution of 1600 µg/ml was diluted in DMSO to solutions having concentrations from 200 µg/ml to 50 µg/ml. These solutions were diluted 1:100 in RPMI-1640 (GiBCO®, by Life Technology) containing 2% glucose, 3-(N-morpholino) propanesulfonic acid (MOPS, by SIGMA) without $NaHCO_3$, to concentrations from 2 µg/ml to 0.5 µg/ml.

Negative controls of water, DMSO and water+DMSO were included in the experiment.

(B) For synergy studies, further solutions of econazole, miconazole, clotrimazole and fluconazole nitrate having concentrations from 100 µg/ml to 0.049 µg/ml were prepared in RPMI-1640 as disclosed in paragraph 1.3.1(A).

Also, further solutions of benzydamine having concentrations from 1 mg/ml to 0.25 mg/ml were prepared in RPMI-1640 as disclosed in paragraph 1.3.1(A). Moreover, the solution of benzydamine with a concentration of 1 mg/ml was further diluted 1:1.43 with RPMI-1640 to concentration of 0.7 mg/ml.

1.3.2 Susceptibility Testing

Microdilution plates containing wells with a nominal capacity of about 300 µL/well were used.

The *Candida* strains suspensions prepared as described in paragraph 1.1 were grown on Sabouraud's agar medium SDA (Oxoid). Colonies were diluted in phosphate-buffered saline (PBS) and suspensions were adjusted to approximately $1-5 \times 10^5$ CFU/ml using Mc Farland 0.5 standard and reading the optical density at 550 nm.

A standard inoculum was prepared by suspending single colonies from a second subculture of *Candida* strains, to achieve an optical density similar to the 0.5 McFarland standard (about $1-5 \times 10^5$ CFU/ml).

(A) For the calculation of the MIC, microdilution plates containing in each well 100 µl of each solution of the active ingredients obtained as described in paragraph 1.3.1(A) were prepared. The wells were then inoculated with 100 µl of *Candida* strains suspensions obtained as disclosed above containing $1-5 \times 10^5$ CFU/ml.

In each well, the final inoculum density and the final concentration of the active ingredients was half of that used (i.e. the final inoculum density was $0.5-2.5 \times 10^5$ CFU/ml, the concentration of econazole and miconazole was from 50 µg/ml to 0.39 µg/ml, the concentration of clotrimazole was from 6.25 µg/ml to 0.098 µg/ml, the concentration of fluconazole was from 50 µg/ml to 3.125 µg/ml and the concentration of benzydamine was from 0.5 mg/ml to 0.0625 mg/ml).

Wells containing 100 µl of amphotericin B inoculated with 100 µl of the same *Candida* suspensions were used as positive control.

Wells containing 100 µl of water, DMSO and water+DMSO and sterile drug-free medium inoculated with 100 µl of the same *Candida* suspensions were used as negative control.

The microdilution plates were incubated for 48 hours at 35° C.

(B) For synergy studies, microdilution plates containing in each well 50 µl of each solution of econazole and miconazole and 50 µl of each solution of benzydamine, obtained as disclosed in paragraph 1.3.1(B), were prepared. Then, the wells were inoculated with 100 µl of the $1-5 \times 10^5$ CFU/ml *Candida* suspensions. In each well, the final inoculum density was half of that used (i.e., $0.5-2.5 \times 10^5$ CFU/ml) and the final concentration of the active ingredients was a quarter of that used (i.e., the concentration of econazole and miconazole was from 25 µg/ml to 0.098 µg/ml, the concentration of clotrimazole was from 0.78 µg/ml to 0.049 µg/ml, the concentration of fluconazole was from 25 µg/ml to 3.125 µg/ml and the concentration of benzydamine was from 0.25 mg/ml to 0.0625 mg/ml and 0.175 mg/ml).

The microdilution plates were incubated for 48 hours at 35° C.

1.4 Calculation of MIC

The lowest concentration of drug that produced a complete inhibition of growth for a certain *Candida* strain was regarded as the minimal inhibitory concentration (MIC) for said strain.

The MIC value for *C. lusitaniae* ATCC® 34449 was obtained with the agar dilution method disclosed in paragraph 1.2.

The MIC values for *C. albicans* ATCC® MYA-427, *C. tropicalis* ATCC® 750, *C. albicans* ATCC® 10231, and *C. albicans* ATCC® MYA-574 fluconazole resistant were obtained with the broth dilution method disclosed in paragraph 1.3.

The MIC values of econazole nitrate, miconazole nitrate, clotrimazole nitrate, fluconazole nitrate and benzydamine for the tested *Candida* strains are disclosed in the following table 1.

TABLE 1

| | *Candida* strains | | | | |
|---|---|---|---|---|---|
| Active ingredient | *C. lusitaniae* ATCC® 34449 | *C. albicans* ATCC® MYA-427 | *C. tropicalis* ATCC® 750 | *C. albicans* ATCC® 10231 | *C. albicans* ATCC® MYA-574 fluconazole resistant |
| Econazole nitrate (µg/ml) | 1.56 | 25 | 12.5 | 25 | 25 |
| Miconazole nitrate (µg/ml) | — | 25 | 6.25 | 6.25 | 50 |
| Clotrimazole nitrate (µg/ml) | — | — | 6.25 | 0.025 | — |
| Fluconazole nitrate (µg/ml) | — | — | 50 | 3.125 | — |
| Benzydamine (mg/ml) | 0.5 | 0.5 | 0.5 | 0.5 | 0.5 |
| Amphotericin B (µg/ml) | — | — | — | 0.5 | — |
| Water | n/a | n/a | n/a | n/a | n/a |
| DMSO | n/a | n/a | n/a | n/a | n/a |
| Water + DMSO | n/a | n/a | n/a | n/a | n/a |

Water, DMSO and water + DMSO used as negative controls showed no inhibitory effect (n/a).

1.5 Synergistic Effect

The fungicidal activity of the combination of benzydamine and econazole nitrate was evaluated against *C. lusitaniae* ATCC® 34449 in Sabouraud agar, with the agar dilution method disclosed in paragraph 1.2.

The synergistic effect of the combinations comprising benzydamine and econazole nitrate was evaluated by calculating the fractional inhibitory concentration (FIC), in accordance with Meletiadis J. et al. in Antimicrobial Agents and Chemotherapy, February 2010, p. 602-609.

The FIC values compared the antimycotic activity of the combination comprising benzydamine and econazole nitrate with the antimycotic activity of each of the active ingredients tested alone.

The FIC values for the combinations comprising benzydamine and econazole nitrate ($FIC_{[combination\ b+e]}$) were calculated for each *Candida* strain using the following equation:

$$FIC_{[combination\ b+e]} = FIC_{[b]} + FIC_{[e]}$$

wherein:

$FIC_{[b]}$ is the fractional inhibitory concentration of benzydamine with respect to a specific *Candida* strain, calculated as the ratio between the MIC of benzydamine in the presence of a sub-MIC amount of econazole ($MIC_{(b+e)}$) and the MIC of benzydamine alone ($MIC_{(b)}$), as follows:

$$FIC_{(b)} = \frac{MIC(b+e)}{MIC(b)}$$

$FIC_{[e]}$ is the fractional inhibitory concentration of econazole with respect to a specific *Candida* strain, calculated as the ratio between the MIC of econazole in the presence of a sub-MIC amount of benzydamine ($MIC_{(e+b)}$) and the MIC of econazole alone ($MIC_{(e)}$), as follows:

$$FIC_{(e)} = \frac{MIC(e+b)}{MIC(e)}$$

Synergy was defined as a FIC lower than 0.5 according to Meletiadis J. et al., Antimicrobial Agents and Chemotherapy, February 2010, p. 602-609.

TABLE 2

| | concentration of benzydamine (mg/ml) | | | |
|---|---|---|---|---|
| | 0.25 | 0.175 | 0.125 | 0.0625 |
| concentration of econazole nitrate (µg/ml) | 0.78 | no growth | no growth | no growth | G |
| | 0.39 | no growth | no growth | no growth | — |
| | 0.195 | no growth | no growth | no growth | — |
| | 0.098 | no growth | G | G | — |

In the above Table, the letter "G" indicates that growth of *C. lusitaniae* ATCC® 34449 was observed.

The FIC for the combination of benzydamine and econazole nitrate ($FIC_{[combination\ b+e]}$) was calculated with the equation disclosed above:

$FIC_{[b]} = 0.125/0.5 = 0.25$ $FIC_{[e]} = 0.098/1.56 = 0.0628$ $FIC_{[combination\ b+e]} = 0.0628 + 0.25 = 0.3128$ The above results demonstrated that when the active ingredients benzydamine and econazole nitrate were associated at sub-MIC concentrations, a synergistic fungicidal activity against *C. lusitaniae* ATCC® 34449 was observed.

The following examples 2 to 5 summarize the results obtained for other *Candida* strains.

Example 2

The fungicidal activity of benzydamine and econazole or miconazole nitrate was evaluated against *C. albicans* ATCC® MYA-427 in RPMI-1640 with the broth dilution method disclosed in paragraph 1.3.

The results are summarized in Table 3.

TABLE 3

| | | concentration of benzydamine (mg/ml) |
|---|---|---|
| | | 0.125 |
| concentration of econazole nitrate (µg/ml) | 3.125 | no growth |
| | 1.56 | no growth |
| | 0.78 | G |
| concentration of miconazole nitrate (µg/ml) | 3.125 | no growth |
| | 1.56 | no growth |
| | 0.78 | no growth |
| | 0.39 | G |

G = growth was observed

The above data clearly show that the combination with benzydamine allowed to reduce the MIC of econazole nitrate from 25 µg/ml as shown in Table 1 to 1.56 µg/ml and the MIC of miconazole nitrate from 25 µg/ml as shown in Table 1 to 0.78 µg/ml.

Example 3

The fungicidal activity of benzydamine and econacole or miconazole nitrate was evaluated against *C. Tropicalis* ATCC® 750 in RPMI-1640, with the broth dilution method disclosed in paragraph 1.3.

The results are summarized in Table 4.

TABLE 4

| | | concentration of benzydamine (mg/ml) |
|---|---|---|
| | | 0.175 |
| concentration of econazole nitrate (µg/ml) | 1.56 | no growth |
| | 0.78 | G |
| | 0.39 | G |
| concentration of miconazole nitrate (µg/ml) | 0.78 | no growth |
| | 0.39 | G |
| | 0.195 | G |

G = growth was observed

The above data clearly show that the combination with benzydamine allowed to reduce the MIC of econazole nitrate from 12.5 µg/ml as shown in Table 1 to 1.56 µg/ml and the MIC of miconazole nitrate from 6.25 µg/ml as shown in Table 1 to 0.78 µg/ml.

Example 3a

The fungicidal activity of benzydamine and clotrimazole or fluconazole nitrate was evaluated against *C. Tropicalis*

ATCC® 750 in RPMI-1640, with the broth dilution method disclosed in paragraph 1.3.

The results are summarized in Table 4a.

TABLE 4a

|  |  | concentration of benzydamine (mg/ml) 0.175 |
|---|---|---|
| concentration of clotrimazole nitrate (µg/ml) | 0.390 | no growth |
|  | 0.195 | no growth |
|  | 0.098 | no growth |
|  | 0.049 | G |
| concentration of fluconazole nitrate (µg/ml) | 25 | no growth |
|  | 12.5 | no growth |
|  | 6.25 | no growth |
|  | 3.13 | G |

G = growth was observed

The above data clearly show that the combination with benzydamine allowed to reduce the MIC of clotrimazole nitrate from 6.25 µg/ml as shown in Table 1 to 0.098 µg/ml and the MIC of fluconazole nitrate from 50 µg/ml as shown in Table 1 to 6.25 µg/ml.

The FIC for the combination of benzydamine and clotrimazole nitrate ($FIC_{[combination\ b+c]}$), calculated with the equation disclosed above, resulted to be 0.37.

The FIC for the combination of benzydamine and fluconazole nitrate ($FIC_{[combination\ b+f]}$), calculated with the equation disclosed above, resulted to be 0.48.

Example 4

The fungicidal activity of benzydamine and econazole or miconazole nitrate was evaluated against *C. Albicans* ATCC® 10231 in RPMI-1640, with the broth dilution method disclosed in paragraph 1.3.

The results are summarized in Table 5.

TABLE 5

|  |  | concentration of benzydamine (mg/ml) 0.125 |
|---|---|---|
| concentration of econazole nitrate (µg/ml) | 6.25 | no growth |
|  | 3.125 | no growth |
|  | 1.56 | G |
| concentration of miconazole nitrate (µg/ml) | 3.125 | no growth |
|  | 1.56 | no growth |
|  | 0.78 | G |

G = growth was observed

The above data clearly show that the combination with benzydamine allowed to reduce the MIC of econazole nitrate from 25 µg/ml as shown in Table 1 to 3.125 µg/ml and the MIC of miconazole nitrate from 6.25 µg/ml as shown in Table 1 to 1.56 µg/ml.

Example 5

The fungicidal activity of benzydamine and econazole or miconazole nitrate was evaluated against fluconazole resistant *C. Albicans* ATCC® MYA-574 in RPMI-1640, with the broth dilution method disclosed in paragraph 1.3.

The results are summarized in Table 6.

TABLE 6

|  |  | concentrations of benzydamine (mg/ml) | | |
|---|---|---|---|---|
|  |  | 0.25 | 0.125 | 0.0625 |
| concentration of econazole nitrate (µg/ml) | 12.5 | no growth | no growth | — |
| concentration of miconazole nitrate (µg/ml) | 25 | no growth | no growth | no growth |
|  | 12.5 | no growth | no growth | — |

G = growth was observed

The above data clearly show that the combination with benzydamine allowed to reduce the MIC of econazole nitrate from 25 µg/ml as shown in Table 1 to 12.5 µg/ml and the MIC of miconazole nitrate from 50 µg/ml as shown in Table 1 to 12.5 µg/ml.

Also, the MIC of benzydamine was reduced from 0.5 mg/ml as shown in Table 1 to 0.125 mg/ml when in combination with econazole and to 0.0625 mg/ml when in combination with miconazole.

Example 6

The following Table 7 shows the formulation of three pharmaceutical compositions according to the present invention in the form of cream for topical application. All values are expressed as percent by weight with respect the total content of the formulation.

TABLE 7

|  | Amount (% w/w) | | |
|---|---|---|---|
| Ingredients | F1 | F2 | F3 |
| Propyl gallate | 0.1 | — | 0.1 |
| EDTA | 0.1 | — | 0.1 |
| Miglyol 812 | 3 | 3 | — |
| Paraffin oil | — | — | 3 |
| Compritol 888 ATO | — | 2 | — |
| Gelot 64 | — | 12 | — |
| Tefose 63 | 18 | — | 18 |
| Labrafil M1944CS | — | — | 3 |
| Labrafil M2130CS | 3 | 3 | — |
| Benzydamine hydrochloride | 0.12 | 0.12 | 0.12 |
| Econazole nitrate | 1 | 1 | 1 |
| Water q.s. | 100 | 100 | 100 |

Miglyol 812: Caprylic/Capric Triglyceride (Sasol Olefin & Surfactants GmbH, Germany
Compritol 888ATO: Glyceryl behenate (Gattefossé SAS, France)
Gelot 64: Mixture of glycerol monostearate and PEG-75 stearate - HLB 10 (Gattefossé SAS, France)
Tefose 63: PEG-6 and PEG-32 palmitostearate/glycol stearate - HLB 10 (Gattefossé SAS, France)
Labrafil M1944CS: Oleoyl polyoxyl-6 glycerides - HLB 9 (Gattefossé SAS, France)
Labrafil M2130CS: Lauroyl macrogol-6 glycerides - HLB 9 (Gattefossé SAS, France)

The cream formulation F1 was tested for evaluating the release of actives after eight hours from application.

Franz diffusion cell experiments were used to analyze the in vitro transdermal flux rates of benzydamine hydrochloride across a substrate membrane. Franz diffusion cells are a common and well known method for measuring transdermal flux rates. The general Franz cell procedure is described in Franz, T. J., Percutaneous absorption: on the relevance of in vitro data. J Invest Derm, 64:190-195 (1975). The following was the methodology used in the present example.

A regenerated cellulose membrane with a porosity of 0.45 µm was used. The membrane was conditioned with a NaCl 0.9% w/v solution before use with the aim to remove air from pores.

The contact area of membrane with product was 0.6 cm$^2$. The receiving compartment was thermostated at 37° C. One gram of cream formulation 1 was applied on the membrane in the donor compartment. Each hour during a period of eight hours, 0.3 ml of a NaCl 0.9% w/v receiving solution was withdrawn and replaced with fresh solution.

The samples collected were analyzed using an HPLC method.

The results were reported as cumulative amount of active ingredient released per unit area versus time. The results of the test are summarized in the following Table 8.

TABLE 8

| Tempo (h) | Release of active (µg/cm$^2$) |
|---|---|
| 0 | 0 |
| 1 | 5.40 |
| 2 | 8.00 |
| 3 | 10.13 |
| 4 | 12.04 |
| 5 | 13.41 |
| 6 | 14.90 |
| 7 | 16.50 |
| 8 | 17.40 |

Example 7

The anti-*Candida* activity of a cream formulation of the present invention containing the same ingredients of cream F1 of table 7 (cream A) was tested in comparison with the activity of Pevaryl® cream, a marketed cream containing 1% of econazole nitrate only (cream B), and placebo (cream C).

*Candida albicans* strain ATCC 10231 was used to investigate the antifungal properties of the creams A to C and in particular to further confirm that the presence of benzydamine had effects on the fungicidal activity of econazole.

To this purpose an agar dilution assay was set up according to Asterholm et al (Acta Derm Venereol 2010; 90: 239-245) so that the cream formulation could be tested. Due to technical needs, the creams had to be diluted in agar so that the final cream concentrations were in the range of from 0.03% to 1% (w/v).

Figure 2:
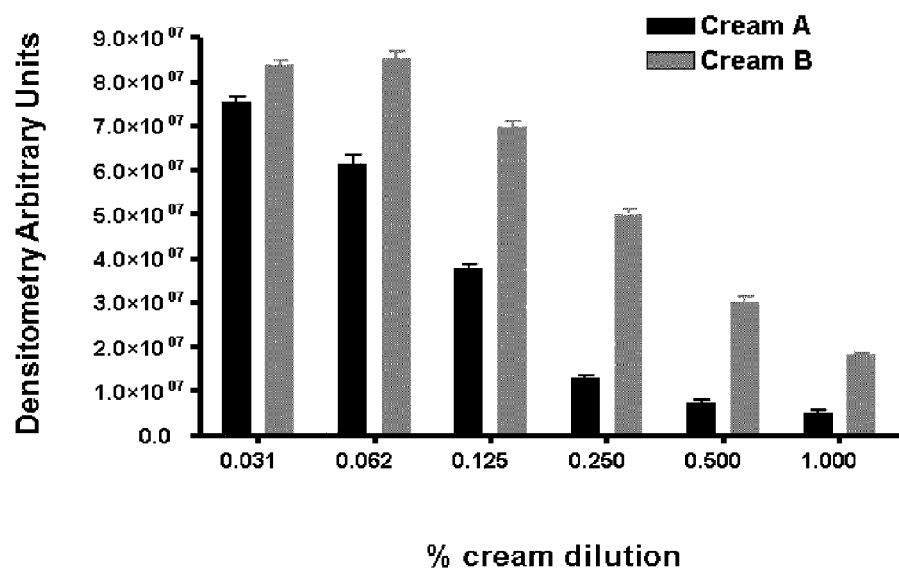
FIG. 2 graphically shows the results of the densitometric analysis performed on plates of FIG. 1.

As reported in FIGS. 1 and 2, visual inspection and densitometric analysis of the plates confirmed that the presence of benzydamine increased the fungicidal activity of econazole. In fact, the data of densitometric analysis showed that a 4-fold lower concentration of cream A was enough to obtain a growth reduction similar to that observed with cream B.

The invention claimed is:

1. A pharmaceutical composition, comprising a synergistic combination of benzydamine and an imidazole-antimycotic or a salt thereof, and at least one pharmaceutically acceptable excipient.

2. The pharmaceutical composition, according to claim 1, wherein said imidazole-antimycotic is selected from the group consisting of bifonazole, butoconazole, chlormidazole, clotrimazole, croconazole, econazole, fenticonazole, ketoconazole, isoconazole, miconazole, neticonazole, omoconazole, oxiconazole, sertaconazole, sulconazole, tioconazole or a salt thereof.

3. The pharmaceutical composition, according to claim 2, wherein said imidazole-antimycotic is selected from the group consisting of bifonazole, butoconazole, clotrimazole, econazole, fenticonazole, ketoconazole, isoconazole, miconazole, omoconazole, sertaconazole, sulconazole, tioconazole or a salt thereof.

4. The pharmaceutical composition, according to claim 3, wherein said imidazole-antimycotic is selected from the group consisting of butoconazole, econazole, fenticonazole, isoconazole, miconazole, sulconazole or a salt thereof.

5. The pharmaceutical composition, according to claim 4, wherein said imidazole-antimycotic is econazole, miconazole or a salt thereof.

6. The pharmaceutical composition, according to claim 1, which is in a form suitable for topical application.

7. The pharmaceutical composition, according to claim 1, wherein said composition is in the form of a cream, ointment, lotion, gel, foam, ovule, prolonged release ovule, vaginal douche, or solution for external use.

8. The pharmaceutical composition, according to claim 7, wherein said composition is in the form of a cream, ointment, lotion, vaginal douche, or solution for external use.

9. The pharmaceutical composition, according to claim 8, wherein said composition is cream or vaginal douche.

10. The pharmaceutical composition, according to claim 1, wherein benzydamine is present in an amount from 0.001 wt. % by weight to 1 wt. % by weight.

11. The pharmaceutical composition, according to claim 1, wherein the imidazole-antimycotic, or a salt thereof, is present in an amount from 0.01 wt. % to 4 wt. %.

12. The pharmaceutical composition, according to claim 2, wherein said pharmaceutical composition is in the form of cream containing one or more emulsifier having a HLB ranging from 6 to 9 and one or more emulsifier having a HLB ranging from higher than 9 to 12.

13. A method of treating *Candida* mycosis, comprising administering an effective amount of a pharmaceutical composition, comprising a synergistic combination of benzydamine and an imidazole-antimycotic or a salt thereof, and at least one pharmaceutically acceptable excipient, to a subject in need thereof.

14. The method according to claim 13, wherein said *Candida* mycosis is caused by a *Candida* species selected from the group consisting of *Candida Albicans, Candida lusitaniae, Candida tropicalis, Candida glabrata, Candida, rugosa, Candida parapsilosis, Candida tropicalis,* and *Candida dubliniensis.*

15. The method according to claim 13, wherein said *Candida* mycosis is mucosal candidiasis, cutaneous candidiasis, onychomycosis, systemic candidiasis, iatrogenic candidiasis, diaper candidiasis, intestinal candidiasis, or *candida* balanitis.

16. The method according to claim 13, wherein said mucosal candidiasis is oral or vulvovaginal.

* * * * *